US005762933A

United States Patent [19]

Mawas et al.

[11] Patent Number: 5,762,933
[45] Date of Patent: Jun. 9, 1998

[54] METHOD FOR PREVENTING AND TREATING GRAFT FAILURE IN A HUMAN PATIENT USING A MONOCLONAL ANTIBODY SPECIFIC FOR LEUCOCYTE FUNCTIONAL ANTIGEN LFA-1

[75] Inventors: Claude Mawas; Daniel Olive, both of Marseilles; Alain Fischer; Claude Griscelli, both of Paris, all of France

[73] Assignee: Institut National de la Sante et de la Recherche Medicale, Paris, France

[21] Appl. No.: 327,829

[22] Filed: Oct. 17, 1994

Related U.S. Application Data

[63] Continuation of Ser. No. 323,243, Mar. 13, 1989, abandoned, which is a continuation of Ser. No. 379, Jan. 5, 1987, abandoned.

[51] Int. Cl.$^6$ .............. A61K 39/395; C07K 16/28; C12N 5/20
[52] U.S. Cl. .............. 424/154.1; 424/143.1; 424/144.1; 424/153.1; 435/343; 435/343.1; 435/343.2; 435/334; 530/388.22; 530/388.7; 530/388.73; 530/388.75
[58] Field of Search .............. 530/388.75, 388.7, 530/388.22; 424/154.1, 130.1, 140.1, 141.1, 143.1, 144.1, 153.1, 172.1, 173.1; 435/240.27, 70.21, 172.2, 326, 332, 334, 343, 343.1, 343.2

[56] References Cited

U.S. PATENT DOCUMENTS

| 4,440,747 | 4/1984 | Neville, Jr. et al. | 424/85.91 |
| 4,443,427 | 4/1984 | Reinherz et al. | 424/1.1 |
| 4,500,637 | 2/1985 | Neville, Jr. et al. | 424/85.91 |
| 4,520,226 | 5/1985 | Neville, Jr. et al. | 424/85.91 |

FOREIGN PATENT DOCUMENTS 0140109  5/1985  European Pat. Off. .

OTHER PUBLICATIONS

Le Mauff, et al. *Effect of Anti–LFAI (COLLa) Monoclonal Antibodies In Acute Rejection In Human Kidney Transplantation*, Aug. 2, 1991, vol. 52, 291–296, No. 2.

Springer et al. "The Lymphocyte Function–Associated LFA–1, CD2, and LFA–3 Molecules: Cell Adhesion Receptors of the Immune System", *Ann. Rev. Immunol.*, 5:223–252 (1987).

Fischer et al., "Prevention of Graft Failure by an Anti–HLFA-1 Monoclonal Antobody in HLA-Mismatcched Bone-Marrow Transplantation", *The Lancet*, Nov. 8, 1986, pp. 1058–1061.

Olive et al., "Human Lymphocyte Functional Antigens", *Human T Cell Clones—A New Approach to Immune Regulation*, (1985) pp. 173–185.

Ferrara et al., "Anti–LFA–1 In Vivo Improves Engraftment and Survival After T Cell Depleted BMT", Blood (1988) 1457-387a.

Fischer et al., "Reduction of Graft Failure by a Monoclonal Antibody (Anti–LFA–1 CDIIa) After HLA Nonidentical Bone Marrow Transplantation in children with Immunodeficiencies, Osteopetrosis, and Panconi's Anemia: A European Group for Immunodeficiency/European Group for Bone Marrow Transplantation Report" Blood, 77:249–256 (1991).

Stoppa et al., "Anti–LFAI Monoclonal Antibody (25.3) for Treatment of Steroid–Resistant Grade III–IV Acute Graft–Versus–Host Disease", *Transplant International— Original Articles*, 4:3–7 (1991).

Cobbold et al. as McMichael Oxford Univ. Press 1987 Lyukocyte typing III 1987.

Todd et al. Lyukocyte Typing 3:95–108 (1986).

Harris et al. Biotechnology 11: 1293–1297 (1993).

Ackermann et al. Biotechnology & Bioengineering 45: 97–106 (1995).

Regnier–Vigouroux et al, Eur. J. Immunol., 16:1385–90, 1986.

Dong worth et al, Eur. J. Immunol., 15:888–892, 1985.

Lanier et al, Eur. J. Immunol., 15:713–718, 1985.

Ritz et al, The Lancet, Jul. 10, 1902, 60–63.

Gougeon et al, Chem Abs., 103:121297F, 1985.

Howard et al, J. Immunol., 136(11), 1986 (Jun.), pp. 4013–4018.

Gromkowski et al, J. Immunol., 134(1), Jan. 1985, 70–77.

Mentzer et al, J. Immunol., 137(1), Jul. 1986, 108–113.

Port et al, J. Immunol., 136(10), 3750–3759, May, 1986.

Campbell, In "Monoclonon Antibody Technology", Chapters 3 Thru 10, 1985, Netherlands Hildreth et al, Eur J. Immunol., 13, 202–8, 1983.

Miller et al, DNAS (USA), 72(12), 5095–8, 1975.

*Primary Examiner*—Lila Feisee
*Assistant Examiner*—Phillip Gambel
*Attorney, Agent, or Firm*—Burns, Doane, Swecker & Mathis, LLP

[57] ABSTRACT

The invention relates to a method for preventing and treating graft failure in humans comprising injecting a specific anti-LFA-1 monoclonal antibody.

6 Claims, No Drawings

METHOD FOR PREVENTING AND TREATING GRAFT FAILURE IN A HUMAN PATIENT USING A MONOCLONAL ANTIBODY SPECIFIC FOR LEUCOCYTE FUNCTIONAL ANTIGEN LFA-1

This application is a continuation, of application Ser. No. 07/323,243, filed Mar. 13, 1989, now abandoned, which is a continuation of application Ser. No. 07/000,379 filed Jan. 5, 1987, now abandoned.

The invention relates to new means and to a method for preventing and treating graft failure in humans.

It more particularly relates to means and a method for preventing and treating organ graft failure, especially in human leucocyte antigen (or HLA)- mismatched bone marrow transplantation.

Bone marrow transplantation is limited by the occurence of graft versus host disease and graft rejection. T cell purging of donor's bone marrow prevents efficiently graft versus host disease in HLA matched and mismatched bone marrow transplantation but leads to a high incidence of graft rejection. This method ablates a delicate balance between donor T cells and residual host immunity. Severe combined immuno-deficiency is the only disease that can be so far cured by T cell depleted HLA-mismatched bone marrow transplantation because of patients' inherent inability to reject grafts.

Therefore, T cell depleted HLA-mismatched bone marrow transplantation needs additional procedure for the prevention of graft failure.

Several approaches have been proposed to prevent graft rejection such as total lymphoid irradiation and increasing the dose of total body irradiation or of chemotherapy.

Such therapies do however lead to increased toxicity and might not be therefore feasible, specially in young patients.

Following another approach, the Inventors have studied the destruction and the blocking in vivo of the function of leucocytes by monoclonal antibodies.

They have then found that anti HLA-1 monoclonal antibody can safely be used to prevent and treat graft rejection in HLA-mismatched bone marrow transplantation.

This discovery is essentially based on the fact that it was shown by the Inventors that patients with congenital LFA-1 deficiency are the only known group of patients who accept HLA-mismatched haploidentical bone marrow from their parents, in absence of a major cellular immunodeficiency.

It is then an object of the invention to provide an anti LFA-1 monoclonal antibody useful in vivo for preventing and treating graft failure without side-effects.

It is another object to provide a new method for preventing and treating organ graft failure, particularly in HLA-mismatched bone marrow transplantation.

The anti LFA-1 monoclonal antibody or anti-LFA-1 mab infused according to the invention to patients for preventing or treating graft failure has the following in vitro properties it does not fix the complement, it blocks the mixed lymphocyte culture (MLR), and partially the PHA-induced proliferation, it blocks T cellular-mediated cytolysis with respect to the population of CD8+anti-class I clones, CD4+anti-class II clones and NK cytolysis assayed on K562, it alters the adhesivity on glass support of polynuclears and the phagocytose of monocytes, it inhibits the fixation of the C3bi component of the complement on its CR3 receptor, it does not react with the leucocyte membrane of children with a congenital immunodeficiency in proteins of the LFA-1-CR$_3$ receptor and Gp150-90 complex, it inhibits antigen-specific T cell helper activity for antibody production, it inhibits partially antigen-induced T cell proliferation.

According to another aspect, the anti-LFA-1 mab used according to the invention has the following characteristics:

it belongs to IgG$_1$ class and is directed against the α subunit of LFA-1, it immunoprecipitates a dimeric glycoprotein consisting of two chains α and β, having a molecular weight of 180 and 90 Kd respectively, it reacts with the α chain of the membrane glycoprotein, its tissular distribution is as follows:
  it reacts with 60% of the peripheral blood cells,
  it reacts with T and B lymphocytes, monocytes, macrophages and polymorphonuclears (neutrophils and eosinophils),
  it reacts with the following T cell lines: MOLT 4, HPB-ALL, CEM,
  it gives a negative reaction with RPMI 8402 line, and 1301,
  it reacts with 60% of the thymocytes.

According to still another aspect, the anti-LFA-1 mab used according to the invention is obtainable by immunizing BALB/c mice with the Tm20 human cytotoxic T cell clone, bearing the following phenotype T3+, T4+, T8–and of HLA-DRw6 specificity, followed by fusion with a murine myeloma.

According to a preferred embodiment of the invention, the mab is a murine anti-LFA-1 mab selected from an hybridoma resulting from the fusion of myeloma 63-Ag 8-653 with BALB/c spleen cells.

Taking into account the therapeutical application of the mab produced, it is particularly preferred to use a subclone having specific qualities, i.e. particularly devoid of mycoplasms, and of murine virus.

A preferred subclone is consituted by 25.3.2 subclone and is obtained from the hybridoma strain.

Advantageously said anti-LFA-1 mab has been proven to be safe in humans and to allow organ engraftment of donor cells as compared to control groups.

Said mab is then useful in vivo as active principle in pharmaceutical compositions.

The pharmaceutical compositions of the invention comprise said mab as purified from ascitic fluids by affinity on protein A and are sterile and devoid of pyrogenic substances, murine virus and mycoplasms.

The purification step on protein A is performed with an ascite liquid containing said mabs, devoid of fibrin and lipids. Advantageously the ascite liquid is equilibrated at a basic pH. Preferably the pH is adjusted to above 8.5. The ascite liquid is contacted with protein A, in an affinity column, protein A being fixed to a support, for example polysaccharides such as those marketed under the trademarks "SEPHAROSE®" and "ULTROGEL®". The mab preparation are recovered by using a buffer having a lower ionic strength than the one used for equilibrating the column.

Preferably, the purification of the mab further comprises an elimination step of the nucleic acids by dialysis against a buffer as PBS (phosphate buffer saline).

The invention relates in particular to solutions of purified mab in a buffer such as PBS, containing 0.5 to 3 mg of mab per ml of buffer, preferably about 1 mg/ml.

The concentrated solutions can be diluted by any usual solute.

The solutions can be constituted from freeze dried powder of mab.

The invention also relates to a method for preventing and treating graft failure which comprises using in vivo said purified mab, advantageously to complement a conditioning regimen. The treatment will be made from about day −15 to day +15.

From the clinical results, it appears recommendable to infuse to the patient every day, from days −3 to day +6, about 0.1 to 5 mg of mab/kg, preferably about 0.2 mg/kg.

Conditioning regimen usually include busulfan, cyclophosphamide and antilymphocyte globulin.

They will however vary depending of the therapeutical indications. For example, in the following indications, the regimen will include:

hereditary diseases: busulfan and cyclophosphamide leukemia: total body irradiation, total lymphoid irradiation, cyclophosphamide and possibly VP16, aracytive, CCNU and nelphalan.

SCID: no treatment

To prevent significant graft versus host disease, it is advantageous to deplete T cells and to give an appropriate therapy.

It is recommended to have a quality of T cell depletion above 2 log. Said quality can be checked by the T cell proliferation method in the presence of I12 and cytofluometry analysis controls in the presence of a standard amount of leads as indicator.

Various methods are available in that respect. A satisfactory depletion of bone marrow T cells is obtained with sheep erythrocyte resetting ex vivo.

Significant graft versus host disease is prevented by further giving a therapy such as cyclosporin-A during several weeks for example, 8 weeks.

Said method has been successful for obtaining stable and functional engraftment, even in patients at high risk for graft rejection.

More particularly said method enables engraftment in HLA- mismatched bone marrow transplantation in patients having a normal or subnormal immunity: acute or chronic leukemia, lymphomas, solid tumors, medullar aplasia, and bone marrow hereditary diseases, including immunodeficiencies and various hereditary disorders.

Rapid hematological recovery has been observed.

The granulocytes reached a level higher than 500/mm$^3$ in 12.7+2 days.

The last platelet infusions were required at 24±11 days.

The regenerating leucocytes were of donor origin in all cases and in some cases chimera were observed.

Side effect was limited to fever.

The results obtained suggest that said treatment may lead to long term maintenance of donor bone marrow cells.

Said method is also useful for preventing and treating graft rejection in organ transplantation, particularly in kidney transplantation.

The invention will be more fully illustrated with reference to the following examples.

The immunological analysis were carried out as follows: Lymphocyte populations were determined by immunofluorescence using specific monoclonal antibodies to CD3 (T3), CD4 (T4), CD8 (T8), and CD2 (T11). B lymphocyte populations were enumerated using anti-antisera to Ig heavy and light chains (1). Mitogen and antigen (Candida albicans, tetanus toxoid, influenza virus), allogenic cell-induced lymphocyte proliferations were performed as previously described (1). Serum Immunoglobulin levels and specific antibody titers to poliovirus, tetanus and diphteria toxoids, bordetella pertusis, influenza virus were measured with usual serological techniques. Chimerism was assessed by karyotyping and quinacrine staining of the Y chromosome in sex mismatched and by HLFA typing in all cases. Ig allotype studies were performed using indirect hemaglutination with specific antisera.

EXAMPLE 1

MONOCLONAL ANTIBODY USED IN VIVO FOR PREVENTING AND TREATING GRAFT FAILURE

Obtention of the ascites

Said mab is obtained by injecting $5 \times 10^6$C of the hybridoma strain (subclone 25.3.2) which results from the fusion of myeloma, 63-Ag 8-653 with spleen cells BALB/c, to mice (BALB/c pretreated with pristan).

Ten days following the injection, the ascite liquid is recovered, the cells are eliminated by centrifugation (4000 g during 10 min.), the supernatant is recovered and frozen.

Purification

All the steps are conducted under sterile conditions. The buffers which are used are prepared with apyrogen, distillated water, and are filtrated and sterilized in an autoclave.

The ascite liquid is unfrozen at 4° C., the fibrin is eliminated by centrifugation at 4000 g during 10 min.

The cleared liquid is filtrated on Millipore AP25 to eliminate traces of lipids. The ascite liquid is then equilibrated to pH 8.5 with a phosphate buffer (1M pH 8.5) by adding 1 volume of said buffer to 9 volumes of ascite.

The purification is performed on protein A (protein A SEPHAROSE CL4B® (Pharmacia) or protein A ULTROGEL® (IBF)). The column is equilibrated with a phosphate buffer (0.1.M pH 8.5) by washing the gel with said buffer (two times the volume of the column).

The volume of ascite loaded on the column must exactly correspond to the dead volume of the column.

After the loading step, the ascite is allowed to incubate in the column during 45 min. The column is then rinsed with a phosphate buffer (0.1.M., pH 8.5) up to total absence of protein in the effluent. The IgG1 25.3.2 are taken down with a citrate buffer (0.1.M, pH 6) and the fractions rich in proteins are recovered.

The column is then regenerated with 0.58% acetic acid 0.15M NaCl and equilibrated with said buffer phosphate.

Biochemical and biological activity control, are carried on. The IgG1 thus purified are analyzed with acrylamid gel SDS using dissociating conditions. After staining, two strips are observed at 50 and 25 kd respectively, corresponding to the heavy and the light chains of the IgG1.

The preparation is also analyzed by FPLC using a mono G column. Only one optical density peak corresponding to IgG1 must be observed.

The IgG1 biological activity is checked by fluorimetry on peripheral blood lymphocytes. The cells are successively incubated with purified antibodies at concentration of 20, 10, 5 µg/ml. The fixation of the antibodies to the cells is revealed by a fluorescent probe (goat antimouse FITC). The results are analyzed with a cytofluorograph.

The material used is a sterile, apyrogenic preparation of mab 25.3–2, purified as disclosed above, diluted in PBS (flask with 0.5 mg in 0.5 ml of PBS).

EXAMPLE 2

CLINICAL EXPERIMENTS a) study group

Seven patients were transplanted between June 1985 and May 1986 (age: between 2 months and 2 years and a half). The original diseases were Wiskott Aldricht syndrome (WAS; n=3), combined immunodeficiency (CID; n=2) and osteopetrosis (n=2). Patients with WAS required bone marrow transplantation because of the severity of the clinical course. One patient had splenectomy, steroids and azathioprine for autoimmune pancytopenia. The second patient with WAS had severe thrombocytopenia with <10,000/ mm$^3$ platelets which could not be corrected by splenectomy. The third patient with WAS had vasculitis. The first patient with CID had multivisceral vasculitis that required the use of steroids and i.v. infusion of cyclosphosphamide.

The patients' age and degree of HLFA incompatibility with the donors are given in table 1 hereinafter All patients in the study group showed significant MLR reactivity against their parent's leucocytes. One patient (n-2) showed HLA-A and HLA-B identity but exhibited the highest degree of MLR reactivity.

b) control group

Seven patients, consecutively transplanted between September 1984 and May 1985, were recorded as historical controls (age: between 3 months and 3 years and a half). These patients were also transplanted for WAS (n=1), CID due to defective synthesis of HLA class II molecules (n=2), CID of unknown origin (n=1); Chediak-Higashi syndrome (CHS; n=2) and osteopetrosis (n=1). Bone marrow transplantation was considered for the severity of their disease. The patient with WAS has a protacted diarrhea requiring parenteral nutrition for months. Patients with CHS were in the acute phase of the disease which was controlled only by chemotherapy consisting of VP16. Patients wiht CID and osteopetrosis were in good condition, but these diseases have poor prognosis.

The pretransplant observations are reported in table 1 hereinafter.

TABLE 1

PATIENTS

| CONTROL GROUP | HLA incompatibility | with donor | STUDY GROUP | HLA incompatibility with donor |
|---|---|---|---|---|
| 1 HLA class II (−) CID | A-B-DR | 1 WAS | | A, B, DR |
| 2 WAS | A-B-DR | 2 Osteopetrosis | | DR |
| 3 CID | A-B-DR | 3 WAS | | A, DR |
| 4 CHS | A-B-DR | 4 Osteopetrosis | | A, B, DR |
| 5 HLA class II (−) CID | A-B-DR | 5 CID | | A, B, DR |
| 6 CHS | DR | 6 CID | | B, DR |
| 7 Osteopetrosis | DR | 7 WAS | | A, B, DR |

CID: Combined ImmunoDeficiency
WAS: Wiskott-Aldrich Syndrome
CHS: Chediak Higashi Syndrome Patients were isolated in a sterile isolator (La Calhene, Paris, France) and received absorbable antibiotics and ketoconazole daily and immunoglobulins (CTS France) weekly for 2 months.

Patients in both study and control groups according to the protocol used for HLA-matched bone marrow transplantation, were given:
 busulfan 4 mg/kg daily from day −9 to −6;
 cyclophosphamide 50 mg/kg from day −5 to −2, and
 antilymphocyte globulins (Merieux, Lyon) 2.5 mg/kg, on days −10, −8, −6, −4,
 cyclosporine 60 days.

In addition, patients from the study group received 0.1 mg/kg of said monoclonal antibody at days −3, −1, +1, +3, +5.

1 ml of serum is taken at day −3 (before injection of the mab), then every day up to day +10 for titration.

The serum is frozen at −20° C. The titration is carried out according to ELISA method using a rabbit mice anti-chain K antibody (Immunotech).

The graft take is evaluated by markers.

Bone marrow T cell depletion was performed in all cases by sheep erythrocyte (E) rosetting method as previously described (1). T cell depletion of donor's bone marrow resulted in a mean infusion of 1.46×10$^8$ cells/kg (range 0.54–2.3×10$^8$) containing 5.5×10$^5$/kg T3+lymphocytes (range 2.7–10×10$^5$) in the seven patients of the study group treated with anti-HLFA-1 antibody.

These data did not differ from those of the control group (mean of total cells 1.3×10$^8$/kg –range 0.4–2.7×10$^{8,}$ mean of T3+lymphocytes 6×10$^5$/kg –range 1.6–13×10$^5$).

EXAMPLE 3

RESULTS a) Study group
Side effects of antiHLFA-1 mab infusion

The administration of anti-HLFA-1 antibody resulted occasionally in fever up to 40° C. Fever was transient. There has been no other side effects.
Hematological recovery Granulocytes reached 500/μl at a mean of 12.7 day (range 10–15 d). The last platelet transfusion was performed between days 10 and 40 (mean 24 days). There has been no secondary blood count abnormalities except in patient n-2 in whom a steroid sensitive auto immune hemolytic anemia occured at day 120.
Engraftment As depicted in table 2 hereinafter, engraftment of donor cells has been proven in all patients of the study group. HLA typing indicated the presence of donor cells in the patients. A mixed chimerism has been observed in two patients either by HLA typing or karyotyping. In both cases the mixed chimerism appears stable, after one year and 6 months respectively.

The evidence for the engraftment of donor bone marrow in patients receiving mab-infusion is given in table 2 hereinafter.
Correction of underlying disease After 60–395 d (mean 225 d), the patients did exhibit the disappearance of clinical and biological manifestations of their underlying disease and are doing well. The specific antigen induced T and B cell responses that were deficient in two patients (n-5 and 6) prior to transplant have been shown to develop following immunizations within 2 to 4 months post transplant.

b) Control group

No donor cells engraftment could be documented in 6 out of 7 patients. On one, a partial lymphocyte engraftment was proven by karyotyping and HLA typing. This patient eventually died from a lymphoma while the proportion of donor lymphocytes was less than 20%. Four patients died from infections in the absence of hematological reconstitution. Finally, in two a complete or partial autologous hematological reconstitution occured. These patients are still alive, in poor condition due to their primary disease progression.

| Patients | HLA typing | Caryotyping | Other clinical evidence of engraftment & |
|---|---|---|---|
| 1 | Donor | Donor | Correction of LD |
| 2 | Mixed | —* | Bone clearing |
| 3 | Donor | — | Increase in |

| Patients | HLA typing | Caryotyping | Other clinical evidence of engraftment & |
|---|---|---|---|
| 4 | Donor | — | platelet size Rising of urine calcium excretion |
| 5 | Donor | Mixed (⅔donor) | Correction of I.D. |
| 6 | Donor | Donor | Correction of I.D. |
| 7 | Donor | — | Correction of thrombocytopenia |

— = not informative
ND = not done
* = Ig allotypes are of donor origin

& = following abnormalities have been corrected following BMT:

patient 1 WAS: Thrombocytopena with small platelet size, T lymphocytopena, Auto antibodies to red cells, PMN and platelets, Low serum IgM, Low antioen-induced lymphocyte proliferation.

patient 2 Osteopetrosis: Anemia, Thrombocytopenia, Presence of immature myeloid cells, Low levels of calcium in serum and urine, Hepato and splenomegaly, Abnormal bone density.

patient 5 CID: Absence of antigen-induced lymphocyte proliferation and skin tests, Absence of antibody production, Eosinophila, Protracted diarrhea.

patient 6 CID: Absence of enticen-induced lymphocyte proliferation and skin tests, Absence of antibody response to vaccinal and infectious antigens, Vasculitis, Diarrhea (Cryptosporidia).

patient 7 WAS: Thrombocytopenia.

Said results demonstrate the safety of using anti-HLFA-1 in vivo.

First, it will be observed that in the patients of the study group hematological recovery was fast, or even faster, than seen in patients receiving fully matched bone marrow without anti-HLFA-1 preconditioning.

The second main observation of the study is the contrasting finding seen in two groups of patients. Both groups have been given busulfan, cyclophosphamide, ALG and cyclosporin therapy and the only major difference between the groups was the infusion of anti-HLFA-1

In the anti-HLFA-1 group rapid bone marrow take was seen in patients. This group includes, to the knowledge of the inventors, the first children successfully receiving haplotype- or HLA-DR mismatched bone marrow transplantation for treatment of Wiskott-Aldrich syndrome and osteopetrosis. These good results are not attributable to a low degree of HLA incompatibility, since the MLR between all recipients and their donors was strong, and since 6/7 donor-recipient pairs differed for at least 2 HLA antigens. Clinical and biological manifestations of their previous diseases have disappeared in all patients.

By contrast, in the conventionally treated group of bone marrow transplantation recipients no lasting dominant bone marrow take was observed and only 2 patients survive without the correction of their underlying immunodeficiency following their autologous reconstitution.

In conclusion, these results indicate that the blocking of the functional HLFA-1 receptor has an important role in bone marrow transplantation.

We claim:

1. A method for preventing and treating graft failure in a patient which comprises administering in vivo to a patient in need of such treatment a graft failure preventing or treating effective amount of an anti LFA-1 monoclonal antibody comprising the following in vitro properties:

said anti LFA-1 monoclonal antibody does not fix complement;

said anti LFA-1 monoclonal antibody blocks the mixed lymphocyte culture and blocks PHA induced proliferation;

said anti LFA-1 monoclonal antibody blocks T cellular-mediated cytolysis with respect to the population of CD8+anti-class I clones, CD4+anti-class II clones and NK cytolysis assayed on K562 cells;

said anti LFA-1 monoclonal antibody inhibits the fixation of the C3bi component of a complement on its CR3 receptor;

said anti LFA-1 monoclonal antibody does not react with a leucocyte membrane of a child with a immunodeficiency in proteins of the LFA-1-CR, receptor and Gp150-90 complex;

said anti LFA-1 monoclonal antibody inhibits antigen-specific T cell helper activity for antibody production;

said anti LFA-1 monoclonal antibody inhibits antigen-induced T cell proliferation; and, said anti LFA-1 monoclonal antibody is directed against an $\alpha$ subunit of LFA-1.

2. A method of claim 1 wherein said anti LFA-1 monoclonal antibody is a murine anti LFA-1 monoclonal antibody selected from a hybridoma resulting from the fusion of myeloma 63-Ag 8-653 with BALB/c mouse spleen cells.

3. The method of claim 2, wherein said hybridoma is a subclone of the hybridoma resulting from the fusion of myeloma 63-Ag 8-653 with BALB/c mouse spleen cells.

4. A method for preventing and treating graft failure in a patient which comprises administering in vivo to a patient in need of such treatment a graft failure preventing or treating effective amount of an anti LFA-1 monoclonal antibody comprising the following in vitro properties:

said anti LFA-1 monoclonal antibody belongs to $IgG_1$ and is directed against a subunit of LFA-1;

said anti LFA-1 monoclonal antibody immunoprecipitates a dimeric glycoprotein consisting of two chains $\alpha$ chain and $\beta$, having a molecular weight of 180 and 90 Kd, respectively;

said anti LFA-1 monoclonal antibody reacts with an $\alpha$ chain of a membrane glycoprotein;

distribution of said anti LFA-1 monoclonal antibody in tissue is as follows:

said anti LFA-1 monoclonal antibody reacts with 60% of peripheral blood cells;

said anti LFA-1 monoclonal antibody reacts with T and B lymphocytes, monocytes, macrophages and polymorphonuclear cells;

said anti LFA-1 monoclonal antibody reacts with the following T cell lines: MOLT-4, HPB-ALL and CEM;

said anti LFA-1 monoclonal antibody gives a negative reaction with RPMI 8402 and 1301 lines; and, said anti LFA-1 monoclonal antibody reacts with 60% of thymocytes.

5. The method of claim 4, wherein said anti LFA-1 monoclonal antibody is a murine anti LFA-1 monoclonal antibody selected from a hybridoma resulting from the fusion of myeloma 63-Ag 8-653 with BALB/c mouse spleen cells.

6. The method of claim 5, wherein said hybridoma is a subclone of the hybridoma resulting from the fusion of myeloma 63-Ag 8-653 with BALB/c mouse spleen cells.

* * * * *